(12) United States Patent
Elyasaf et al.

(10) Patent No.: US 6,175,645 B1
(45) Date of Patent: *Jan. 16, 2001

(54) OPTICAL INSPECTION METHOD AND APPARATUS

(75) Inventors: Emanuel Elyasaf, Rehovot; Ehud Tirosh, Jerusalem, both of (IL)

(73) Assignee: Applied Materials, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/010,570

(22) Filed: Jan. 22, 1998

(51) Int. Cl.[7] ................................. G06K 9/00
(52) U.S. Cl. ............... 382/147; 382/149; 356/239.8; 356/237.4
(58) Field of Search .................... 382/144, 147, 382/148, 149; 324/501, 537; 356/237, 394, 394.5, 237.2, 237.3, 237.4, 237.5, 239.7, 239.8, 238.8; 350/237.47; 348/125, 126

(56) References Cited

U.S. PATENT DOCUMENTS

| | | | |
|---|---|---|---|
| 4,893,346 | * 1/1990 | Bishop | 382/147 |
| 5,309,108 | * 5/1994 | Maeda et al. | 324/501 |
| 5,386,112 | 1/1995 | Dixon | 250/234 |
| 5,563,702 | * 10/1996 | Emery et al. | 356/73 |
| 5,572,598 | 11/1996 | Wihl et al. | 382/144 |
| 5,764,363 | * 6/1998 | Ooki et al. | 356/364 |
| 5,892,579 | * 4/1999 | Elyasaf et al. | 356/239.8 |

FOREIGN PATENT DOCUMENTS

| | | |
|---|---|---|
| 0 819 933 A2 | 1/1998 | (EP) . |
| 0 838 679 A2 | 4/1998 | (EP) . |

* cited by examiner

*Primary Examiner*—Bhavesh Mehta
(74) *Attorney, Agent, or Firm*—Sughrue, Mion, Zinn, Macpeak & Seas, PLLC

(57) ABSTRACT

A method and an apparatus for an optical inspection of an object, having upper and lower faces, so as to detect defects existing on the object. First and second beams of an incident radiation are produced and directed onto the object. A light component of the first incident beam, which is reflected from one face of the object, and a light component of the second incident beam, which is transmitted through the upper and lower faces of the object, are simultaneously sensed. First and second images, formed, respectively by reflected and transmitted light components are acquired and analyzed so as to provide data indicative of the defects.

55 Claims, 7 Drawing Sheets

OPTICAL INSPECTION METHOD AND APPARATUS

FIELD OF THE INVENTION

The present invention is in the field of optical inspection techniques and relates to a method and a system for inspecting patterned objects such as, for example, photomasks, printed circuit boards (PCBs) or the like.

BACKGROUND OF THE INVENTION

There is a great variety of optical inspection systems having a common goal for locating defects existing on the patterned surface of an inspected object. The term "patterned surface" signifies such a surface which is formed with regions having different optical properties in respect of an incident radiation.

An inspection system of the kind specified typically comprises means for illuminating an object to be inspected, acquiring images formed by light reflected from the illuminated object, and image processing. However, if the inspected object is a photomask, flexible printed circuit board (PCB) or the like, whose patterned surface typically comprises transparent and opaque regions, the acquired images formed of light reflected from the illuminated surface are not indicative of such 'defects' as foreign particles, for example, of dirt or dust, which may occasionally be located in the transparent regions. Indeed, it is known that a surface of such particle is not mirror like, and, accordingly, light returned from the particle is irregularly reflected, scattered light. The problem is very essential when using the photomask as a phototool in PCB, graphic arts and printing industries.

There have recently been developed methods and systems wherein the inspection is performed by means of illuminating an object and acquiring and processing images formed of reflected and transmitted beams of light. Such systems are disclosed, for example, in U.S. Pat. Nos. 5,572,598 and 5,563,702. The systems in both patents employ a so-called 'scanning technique', wherein an illuminating laser beam is generated and focused onto a pixel defining spot on the surface of an object to be inspected. The illuminated beam is deflected in an oscillatory fashion so as to sweep the spot across the inspected surface. The system is adapted for three different modes of operation. According to the first and second modes, so-called "Transmitted Light Inspection Mode" and "Reflected Light Inspection Mode", the object is point-by-point inspected by means of detecting either transmitted or reflected light, respectively. These modes of operation are timely separated. The third mode of operation, which is aimed at defects classification, is based on detecting both reflected and transmitted beams of light. A single laser beam of incident radiation is directed onto the patterned surface of an object through light deflection means and is either reflected or transmitted, or partly reflected and partly transmitted by the object. This intensity of the incident beam is determined before its interaction with the object. Two separate detectors are accommodated at opposite sides of the object and detect transmitted and reflected beams resulting from this interaction. To this end, the system comprises separate directing optics for receiving the transmitted and reflected beams, respectively, and directing them onto the detectors.

This approach is based on that the interaction of an incident beam with an object to be inspected causes changes in beam's intensity, which changes depend on reflectivity and transmission of the respective region of the object. Hence, by appropriately detecting the intensities of the incident beams and reflected and transmitted beams, respectively, before and after the interaction, each inspectable point, or pixel, on the surface can be represented in a so-called 'T-R space', namely by a point with coordinates corresponding to the transmitted and reflected signal values produced at that point.

However, the system requires very complicated arrangements for illuminating and collecting optics. Indeed, the illuminating arrangement should be provided with the light deflection means and detector appropriately accommodated in the optical path of the incident beam so as to determine the beam intensity prior to the interaction with the object. This complicates and extends the optical path of the incident beam. Moreover, the use of a single beam of incident radiation results in an unavoidable requirement for locating the collecting optics, as well as the detectors for sensing the reflected and transmitted beams, at opposite sides of the object.

SUMMARY OF THE INVENTION

It is an object of the present invention to provide novel method and apparatus for automatic optical inspection of an object by means of detecting reflected and transmitted light components of an incident radiation.

There is provided, according to one aspect of the invention, a method for an optical inspection of an object, having upper and lower face, so as to detect defects existing on the object, the method comprising the steps of;

(a) providing first and second beams of an incident radiation;

(b) directing the first beam of the incident radiation onto the object and sensing a light component reflected from one face of the object;

(c) directing the second beam of the incident radiation onto the object and sensing a light component transmitted through the upper and lower faces of the object;

(d) simultaneously acquiring first and second images of the object, wherein the first image is formed by the reflected light component and the second image is formed by the Transmitted light component; and (e) analyzing said first and second images so as to provide data indicative of said defects.

The term "defects" used herewith signifies certain undesirable conditions of the object such as, for example, existence of foreign particles located on the object.

Thus, the idea of the present invention is based on the following main features. The first and second beams of incident radiation are produced and directed towards the object for focusing them onto the upper face. It is understood that, generally, each of the incident beams can be both reflected and transmitted by the different regions of the object. In other words, each of the incident beams, depending on the region of its interaction with the object, may be partly transmitted and partly reflected resulting in, respectively, transmitted and reflected light components. To this end, what is actually detected by two image sensors are, respectively, that light component of the first incident beam which is reflected from the object and that light component of the second incident beam which is transmitted through the object.

Generally, the first and second incident beams can be directed onto the object from the same side thereof, that is from either the upper or the lower face. In this case the sensors and associated directing optics are located. at opposite sides of the object. It should be noted that it is advantageous to illuminate the object from opposite faces. This enables the sensors to be placed at one side of the object and, accordingly, a common directing optics to be employed for receiving both the reflected and transmitted light components and directing them onto the respective sensors.

Thus, the reflected and transmitted light components are, preferably, directed onto the different sensors via a common optical system appropriately accommodated in the optical paths of the both light components. It is understood that, accordingly, means should be provided for successfully separating the different light components so as to be sensed by the different image sensors. To this end, two alternating embodiments of the invention are exemplified.

According to one embodiment, the first and second beams of the incident radiation are simultaneously directed onto different portions of the object. More specifically, they illuminate, respectively, first and second spaced-apart, parallel, identical strips of the upper face. The relationship between the two illuminated strips and the common optical system is such that the strips extend symmetrically relative to the optical axis of the common optical system. The optical system actually projects the strips onto the first and second image sensors, which are, preferably, line sensors. Hence, a pair of spaced, parallel lines of the object is imaged, It is understood that the dimensions of the line are defined by a field of view of the image sensor, the width a of the line being substantially smaller than that of the illuminated strip. The space between the two illuminated strips is adjusted so as to minimize an overlap region between the two images. The space d between the two imaged lines satisfies the following condition:

$$d = n \cdot a$$

wherein n is an integer such that not.

According to an alternative embodiment of the invention, the first and second beams of the incident radiation illuminate the same portion of the upper face, which portion is in the form of a strip. To this end, the first and second beams of the incident radiation are formed of light having either different wavelengths, or different polarizations. In the case of different wavelengths, the common optical system comprises a suitable beam splitter, for example, a dichroic beam splitter. In the case of the different polatizations, the common optical system is provided with appropriate beam polarizer device based, for example, on a double refraction effect.

The first and second beams of the incident radiation may be produced by either two light sources, or by a single light source adapted for generating a beam of light. If the single light source is employed, the generated beam is directed towards the object via a beam splitter, which splits it into the first and second beams of the incident radiation.

Preferably, the image sensors are of a kind adapted to receive a light signal and provide an electric output representative thereof. For example, charge coupled device (CCD) cameras, or bidirectional time delay integration (IDI) sensor may be employed.

In order to successively inspect the whole object, it is supported for sliding movement within an inspection plane along two orthogonally oriented axes. It is appreciated that in order to allow for so-called "double side" illumination, the object may be supported on a transparent slab, or, alternatively, on a frame supporting solely the periphery region of the object. As a result of the inspection, each point on the upper face of the object is represented by so-called 'reflected' and 'transmitted' images. Comparing these images to each other enables to locate the defects, if any, on the object. For that purpose, the output signals provided by the image sensors are transmitted to a processor operated by a suitable software for comparing the first and second images to each other.

According to another aspect of the present invention there is provided an apparatus for an optical inspection of an object, having upper and lower faces, so as to detect defects existing on the object, the apparatus comprising:

(i) an illumination system for producing first and second beams of an incident radiation and simultaneously directing them onto the object;

(ii) a sensing system mounted for sensing a light component of the first incident beam reflected from the upper face and a light component of the second incident beam transmitted through the upper and lower faces of the object, and for providing output signals representative thereof, (iv) a light directing system accommodated in optical paths of the reflected and transmitted light components for directing them onto the sensing system; and (v) a processor coupled to the sensing system for receiving and analyzing said output signals representative of the reflected and transmitted light components and for providing data indicative of said defects.

Thus, the present invention enables to inspect an object by simultaneously illuminating it by two incident beams of light and detecting reflected and transmitted light components of these incident beams, respectively. In other words, in comparison to the above U.S. patents, each point of the inspected object is represented by both "T-map" and "R-map", i.e. "transmitted image" and "reflected image". This simplifies the analyzing procedure. Additionally, owing to the provision of the common optical system for directing the reflected and transmitted beams onto the different sensors, and the above solutions for successful separation between the reflected and transmitted beams, the construction and operation of the apparatus can be significantly simplified.

More specifically the present invention is used for inspecting a photomask which is typically in the form of a polished transparent substrate whose upper surface has a plurality of spaced-apart regions coated by a thin opaque layer such as, for example, chromium. The upper surface of the photomask represents a pattern in the form of transparent and opaque regions. Defects, which can be detected by the method according to the invention, may also be in the form of through-holes in the opaque regions and/or width variation of these regions. It is understood that the opaque and transparent regions of a photomask would be represented by bright and dark regions in the 'reflected image' and by dark and bright regions, respectively, in the 'transmitted image'. If a foreign particle is located in the transparent region, it will appear as a bright spot on a dark background in the reflected image and vice versa in the transmitted image. If a foreign particle is located in the opaque region, solely the image sensor responsive to the reflected light component will detect it. Such particle will appear as a dimmer spot on the bright background in the reflected image. The other kinds of defects such as, for example, through-holes in the opaque regions or width variation of these regions will be detected by both the reflected and transmitted beams.

BRIEF DESCRIPTION OF THE DRAWINGS

In order to understand the invention and to see how the same may be carried out in practice, several preferred embodiments will now be described, by way of non-limiting example only, with reference to the accompanying drawings, in which.

DETAILED DESCRIPTION OF THE PREFERRED EMBODIMENTS

Figure 1:
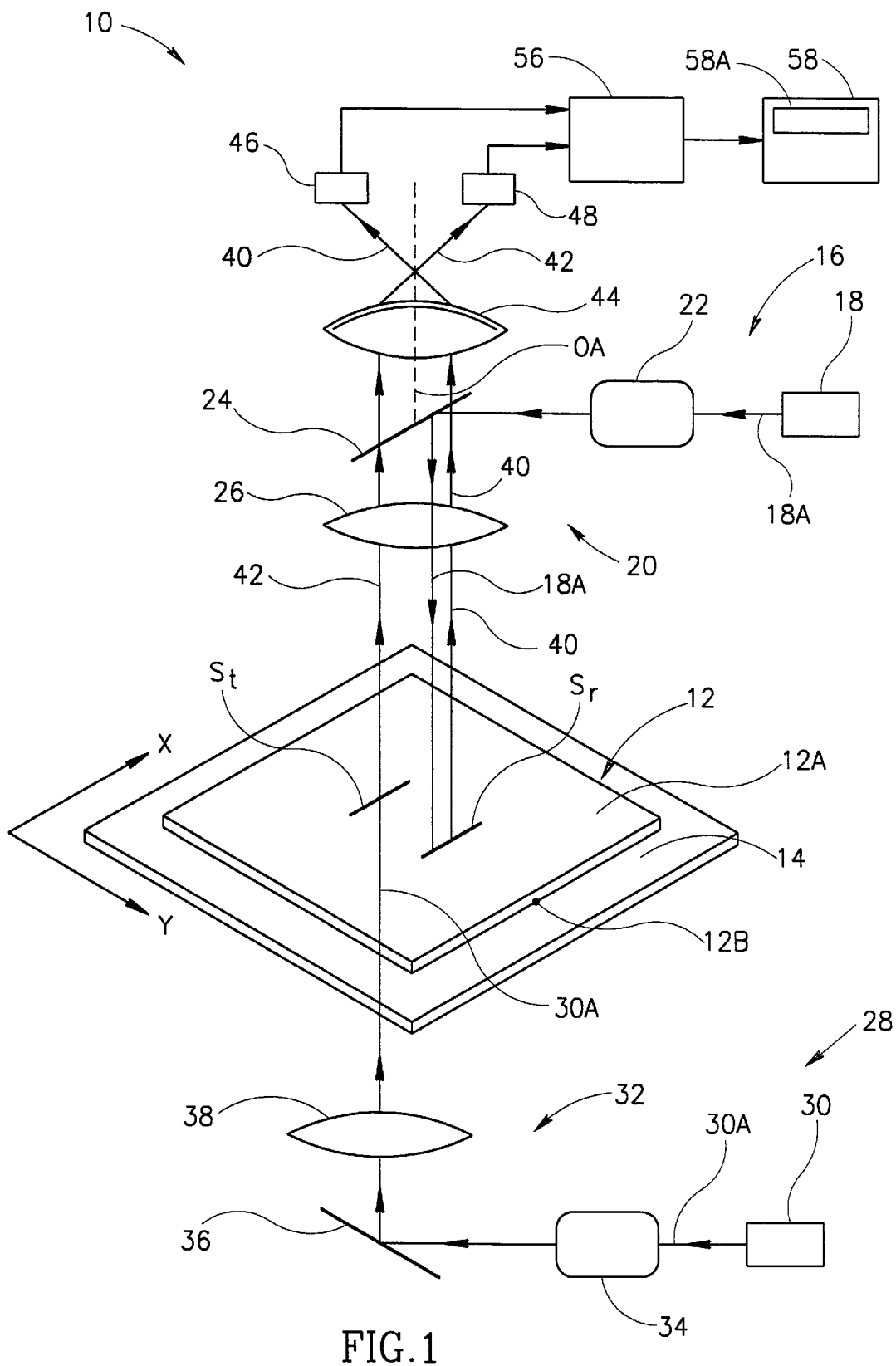
FIG. 1 is a block diagram illustrating the main components of an apparatus for optical inspection of a patterned object, according to one embodiment of the invention.

Referring to FIG. 1, there is illustrated an apparatus, generally designated 10, for inspecting a photomask 12. The propagation of beams of light is shown here schematically solely in order to facilitate the understanding of the main principles of the construction of the apparatus 10. The photomask 12 is typically in the form of a polished transparent substrate having upper and lower surfaces 12a and 12b, respectively. The upper surface 12a is formed with a pattern (not shown) having a plurality of spaced-apart regions coated by a thin opaque layer such as, for example, chromium. In other words, surface 12a is formed with transparent and opaque regions. The photomask 12 is supported at its periphery region on a frame 14 mounted for sliding movement along mutually orthogonal axes x and y. Alternatively, a sliding base formed of a transparent material may be employed for the same purpose of slidingly displacing the photomask 12 within an inspection plane in a manner to provide illumination access to the lower surface 12b.

The apparatus 10 comprises an illumination assembly, generally at 16 mounted at the upper side of the photomask 12 for illuminating its upper surface 12a. The assembly 16 includes a light source 18, producing a beam of light 18a, and an optical system 20, accommodated in the optical path of the beam 18a. The optical system 20 includes an anamorphic optics 22 typically comprising a cylindrical lens or plurality of such lenses, which are not specifically shown, a beam splitter 24 and an objective lens 26. All these components of the optical system 20 are well known per se and, therefore, need not be described in more detail, except to note that they enable a desired shape of the beam 18a to be obtained and focussed onto the photomask 12. As shown, the beam 18a illuminates a strip $S_r$ of the upper surface 12a.

Further provided is an illumination assembly, generally designated 28, mounted at the lower side of the photomask 12 for illuminating its upper surface 12a. Similarly, the assembly 20 includes a light source 30 producing a beam of light 30a, and an optical system 32 accommodated in the optical path of the beam 30a. The optical system 32 comprises an anamorphic optics 34, a mirror 36 and a condenser lens 38. The beam 30a, being transmitted through the transparent lower surface 12b, illuminates a strip $S_t$ of the upper surface 12a. It will be understood that the provision of the mirror 36 is optional and depends solely on the location of the light source 30 relative to the surface 12b.

Figure 2:
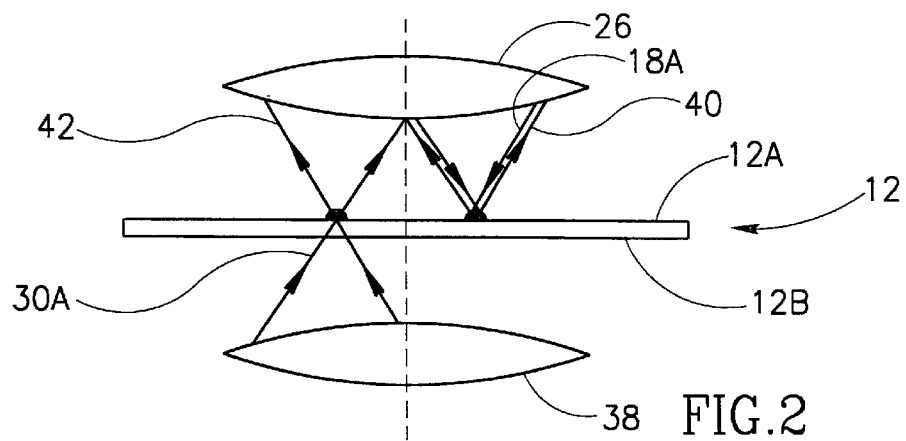
FIGS. 2 and 3 more specifically illustrate the main principles of operation of the apparatus of FIG. 1.

As further schematically shown in FIG. 1 and more specifically in FIG. 2, the beam 18a impinges onto the surface 12a and is reflected from reflective regions, if any, disposed within the strip $S_r$, resulting in a reflected beam 40. The incident beam 30a, being transmitted through the transparent lower surface 12b of the photomask 12, impinges onto the upper surface 12a and is transmitted through transparent regions, if any, within the strip $S_r$, producing a transmitted beam 42.

Figure 3:
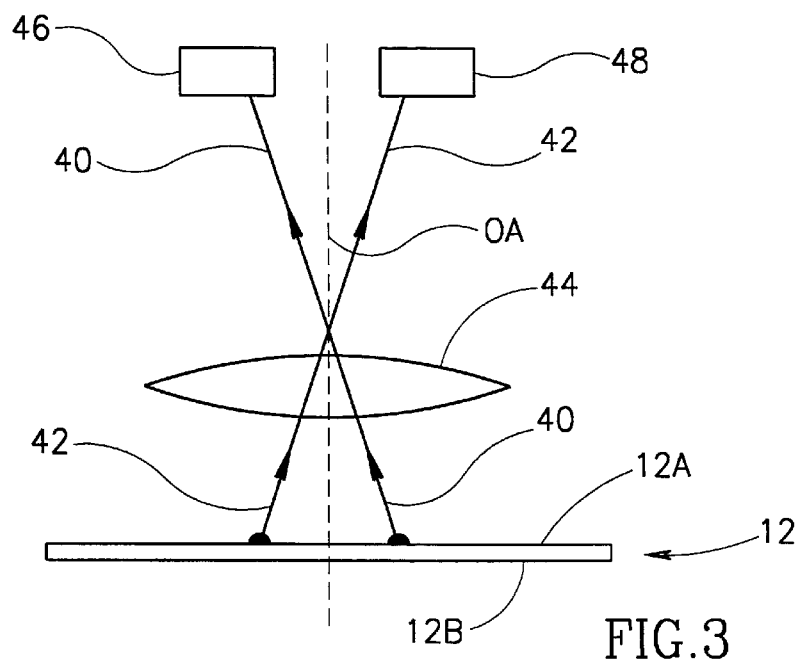

An optical system 44, typically comprising a collecting lens or plurality of such lenses (not shown), is located at the upper side of the photomask 12 so as to be in the optical paths of both the reflected beam 40 and transmitted beam 42. The system 44 has its optical axis shown in dotted line OA. The system 44 directs the beams 40 and 42 onto line sensors 46 and 48, respectively, thereby projecting two geometrically separated strips $S_r$ and $S_t$ into two imaged lines $L_r$ and $L_t$. The image $L_r$ is formed by light reflected from the strip $S_r$ illuminated by the beam 18a, while the image $L_1$ is formed by light transmitted through illuminated strip $S_t$. As more specifically illustrated in FIG. 3, in order to render the image quality at both sensors equal, the configuration is such that the illuminated strips $S_r$ and $S_t$ extend symmetrically relative to the optical axis OA.

It is understood, although not specifically illustrated, that the dimensions of the imaged lines $L_r$ and $L_t$ are defined by the field of view of each of the sensors 46 and 48 and are substantially smaller than those of the strips $S_r$ and $S_t$. The sensors 46 and 48 are of a kind adapted for receiving light signals and generating electrical outputs corresponding thereto such as, for example, a conventional line-type CCD camera.

Figure 4:
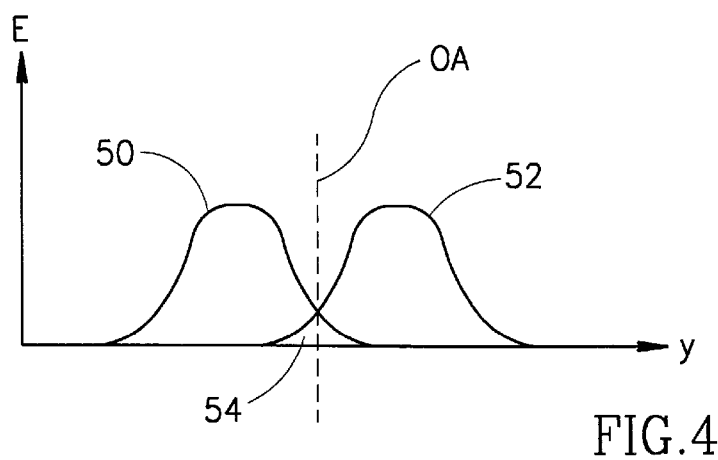
FIG. 4 is a graphic illustration of the main principles of operation of an optical system of the apparatus of FIG. 1.

FIG. 4 illustrates the intensity distributions of the beams 40 and 42 which are in the form of two lobes 50 and 52, respectively. It is appreciated that the spacing between the two illuminated strips $S_r$ and $S_t$ is arranged so as to minimize an overlap region 54, thereby reducing crosstalk between the two images.

Turning back to FIG. 1, coupled to the sensors 46 and 48 is a processor 56 receiving the electrical outputs of the sensors 46 and 48. The processor 56 is operated by suitable software carrying out an image processing technique capable of analyzing the imaged lines $L_r$ and $L_t$ by means of comparing the electrical outputs to each other and of providing information indicative of defects, if any, on the photomask 12. The electrical outputs may also be compared with corresponding reference data which may be stored in a database of the processor 56 or derived from another photomask or from another part of the same photomask being inspected. The construction and operation of the processor 56 do not form a part of the present invention and therefore need not be more specifically described. The information generated by the image processor 56 is output to a computer device 58 and displayed on its screen 58a.

Alternatively, although not specifically shown, the processor 56 and the computer device 58 may be combined in one integral unit. The light sources 18 and 30 may be replaced by a single light source for generating a beam of radiation, in which case the generated beam is directed onto the inspected photomask via a beam splitter so as to be split into two separate beams for illuminating the photomask from opposing sides.

The operation of the apparatus 10 will now be described with reference to FIGS. 5a–5f, partly illustrating images of the upper surface 12a of the photomask 12 during the inspection. Initially, two strips are simultaneously illuminated (not shown) in the above described manner and two lines $Lr_1$ and $Lt_1$ are imaged. The lines $Lr_1$ and $Lt_1$ are identical having the same width a and length b and are aligned in a spaced-apart, parallel relationship along the y axis. A space d between the lines $Lr_1$ and $Lt_1$ is defined as follows:

$$d = n \cdot a \quad (1)$$

wherein n is an integer n≧t, being equal to 1 in the present example.

Figure 5A:
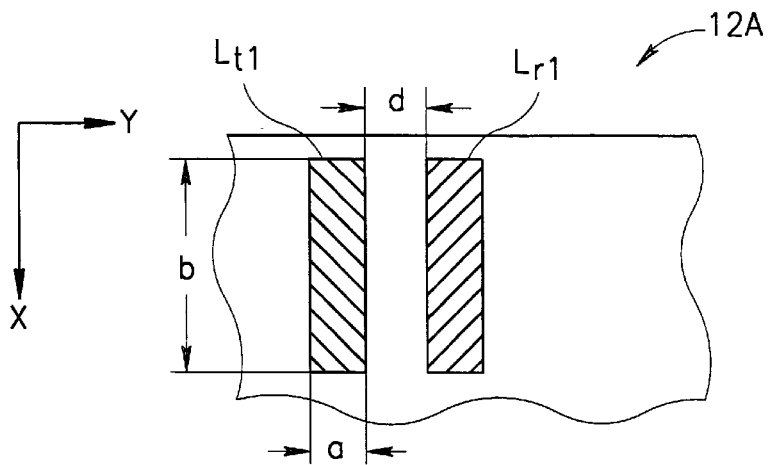
FIGS. 5a to 5f are schematic illustrations of images of the illuminated portion of an upper surface of the object during sequential steps of operation of the apparatus of FIG. 1.
Figure 5B:
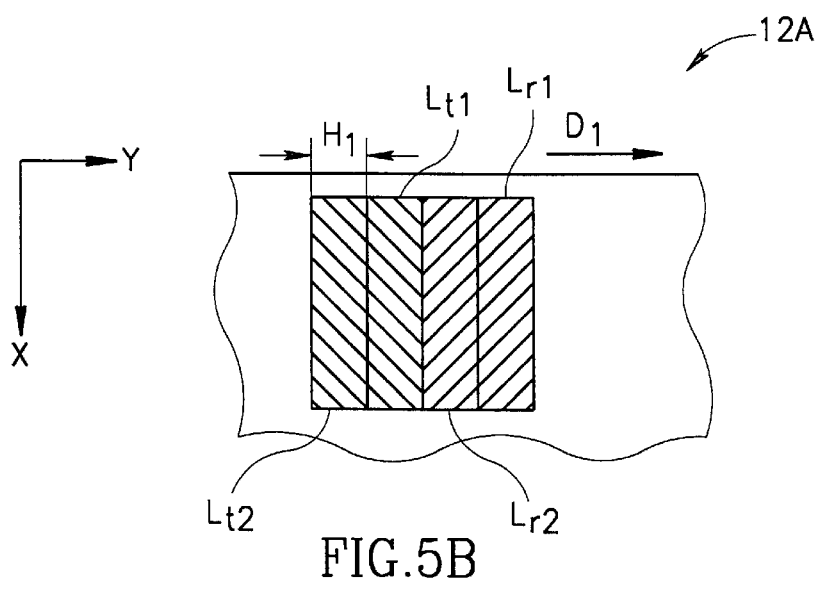
Figure 5C:
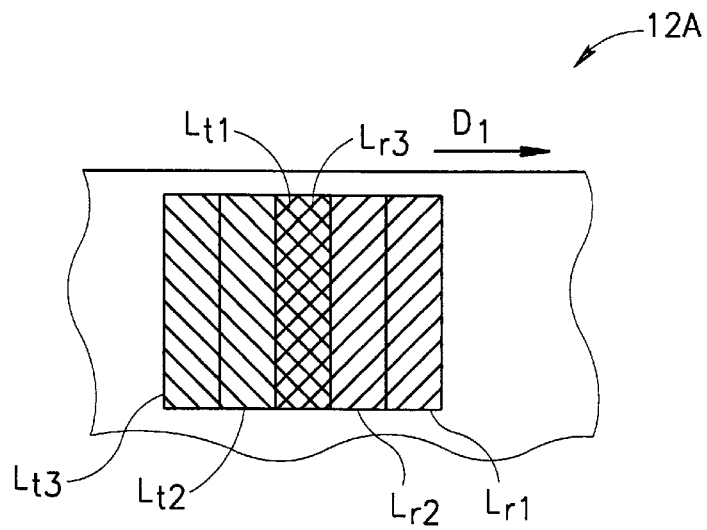
Figure 5D:
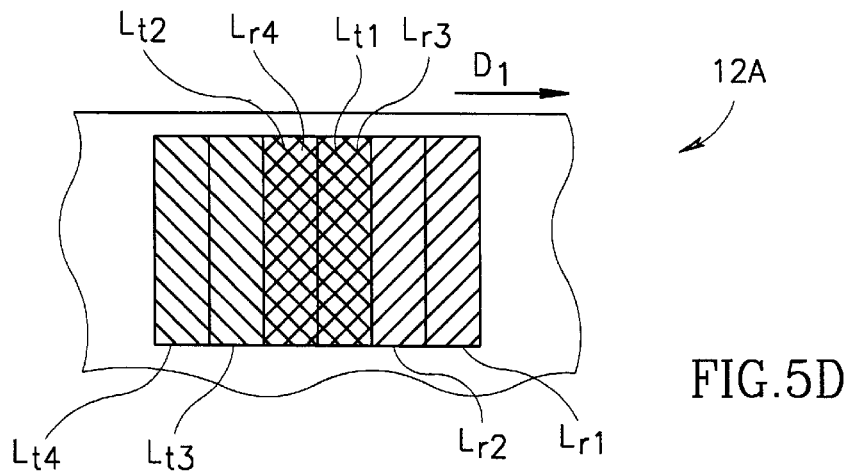
Figure 5E:
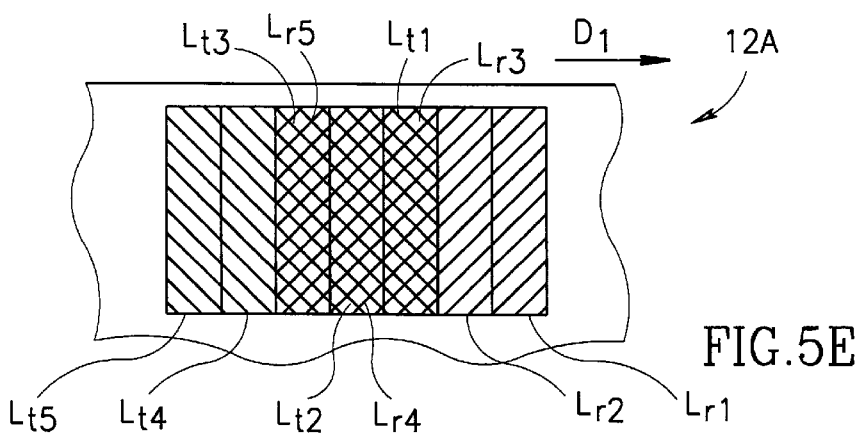
Figure 5F:
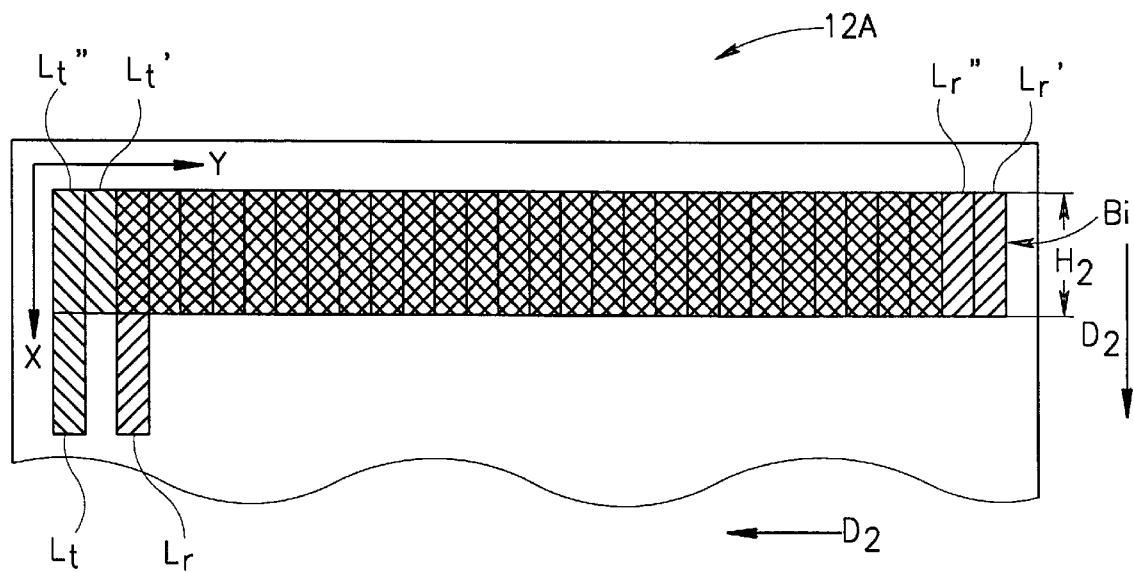

At a next operational stage, the support frame 14 moves the photomask a certain preset step $H_1$ in a direction $D_1$ along the axis y, which step satisfies the following condition:

$$H_1 = n_1 \cdot a \quad (2)$$

wherein $n_1$ is an integer $n_1 \geq 1$, being equal to 1 in the present example. A further pair of lines $Lr_2$ and $Lt_2$ is imaged by the sensors 46 and 48, respectively, and corresponding electrical outputs are transmitted to the processor 56. Meanwhile, the sliding movement of the frame 14 in the direction $D_1$ results in a further displacement of the photomask the same step $H_1$, and a pair of lines $Lr_3$ and $Lt_3$ is imaged. As clearly seen in FIG. 5c, the lines $Lt_1$ and $Lr_3$ coincide, which means that the corresponding strip of the surface 12a has now been sequentially illuminated by the beams 30a and 18a. FIGS. 5d and 5e illustrate, in a self-explanatory manner, the sequential increase of the number of such imaged lines corresponding to those strips illuminated by both beams of the incident radiation.

Hence, a slice, generally at $B_i$, of the surface 12a is strip-by-strip inspected by step-by-step displacing the photomask 12 in the direction $D_1$ along the axis y. It is understood that the beginning of the inspection is stipulated such that the lines $L_r'–L_r''$ and $L_t'–L_t''$ corresponding to those strips illuminated by either of the beams 18a or 30a, respectively, are associated with a so-called 'margin', non-patterned region of the surface 12a.

In order to inspect an adjacent slice $B_{i+1}$ of the surface 12a, the sliding frame 14 is moved a preset step $H_2$ in a direction $D_2$ along tile axis x, which step $H_2$ is defined as follows:

$$H_2 = b \quad (3)$$

Thereafter, the photomask 12 is step-by-step displaced the same distance $H_1$ in a direction $D_3$ along the axis y. As shown, in the pair of simultaneously imaged lines $L_r$ and $L_t$ of the slice $B_{i+1}$ the 'reflected' and 'transmitted' images are located in a reverse relationship relative to the direction of the displacement of the photomask, in comparison to that of the pair of simultaneously imaged lines $L_r$ and $L_t$ of the slice $B_i$. To this end, the image processor 56 is provided with a suitable software for controlling its operation so as to consider the respective changes in the direction of movement of the photomask 12. Additionally, although not specifically shown, optical sensors may be appropriately accommodated at either side of the frame 14.

It is important to note that if a pair of time delay integrated (IDI) sensors is employed as the imaging sensors 46 and 48, they should be of the so-called 'bi-directional' kind. The construction and operation of such a 'bi-directional' TDI sensor are well known per se and do not form a part of the present invention.

Figure 6A:
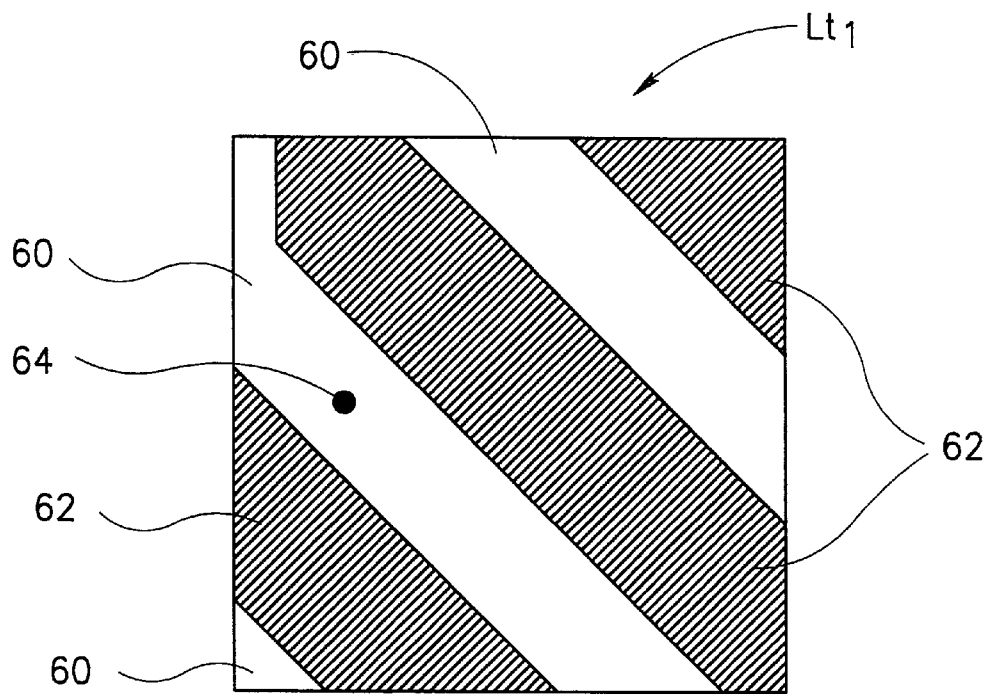
FIGS. 6a and 6b are schematic illustrations of two images of a region of the upper surfaces of the object.
Figure 6B:
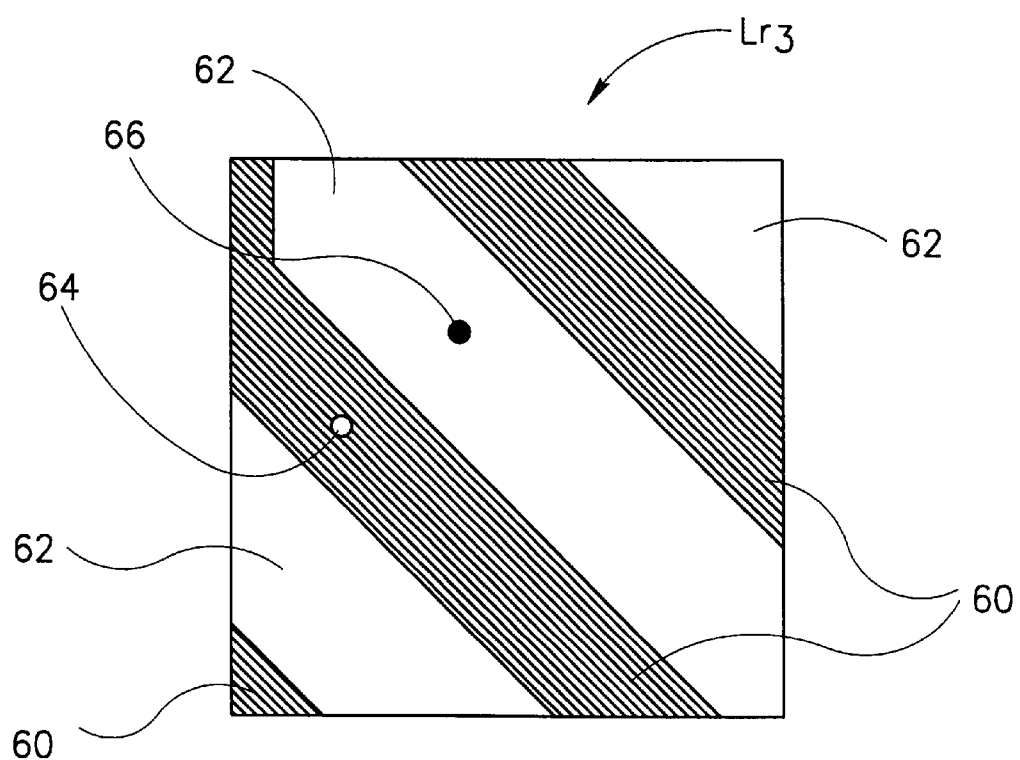

Turning now to FIGS. 6a and 6b, there are more specifically illustrated the imaged lines $Lt_1$ and $Lr_3$, which correspond to the same illuminated strip on the surface 12a, which strip is sequentially illuminated by the beams 30a and 18a. It is assumed that the portion of the upper surface within the illuminated strip includes both transparent and opaque regions, generally designated 60 and 62, and that foreign particles 64 and 66 are located, respectively, in the transparent and opaque regions 60 and 62. As clearly shown, the transparent and opaque regions 60 and 62 are in the form of bright and dark areas, respectively, in the 'transmitted' image $Lt_1$ (FIG. 6a), while being in the form of dark and bright areas, respectively, in the 'reflected' image $Lr_3$ (FIG. 6b). As for the foreign particles, it is known that a surface of such particle is not mirror like, and, accordingly, fight returned from the particle is irregularly reflected, scattered light. Therefore, both the transmitted and reflected beams 40 and 42 are indicative of the existence of the particle 64 located within the transparent region. The particle 64 appears as light fall-off, i.e. dark spot on the bright background 60, in the 'transmitted' image $Lt_1$ and as a brighter spot on the dark background 60 in the 'reflected' image $Lr_3$. The existence of the particle 66 located on the opaque region 62 may be detected solely by the reflected beam 40, appearing as a dimmer spot on the bright background in the 'reflected' image $Lr_3$.

It is also appreciated that, should the plane of location of the particle 64 be identified, namely the upper or the lower surface of the photomask 12, this may be achieved by slightly shifting the upper Surface 12a along the axis OA, so as to be out of the focal plane, and detecting the changes in the electrical output. Additionally, it is understood, although not specifically shown, that both the 'reflected' and 'transmitted' images will be indicative of such 'defects' as through-holes in the opaque regions and missed chromium coating presenting a so-called 'width variation defect'.

During the movement of the photomask 12 along the axes y and x as described above, the processor 56, to which the electrical signals generated by the sensors 46 and 48 are continuously fed, analyzes these electric signals and produces data indicative of the condition of the photomask 12. The processed data may be in the form of a list showing in respect of each 'defect' its type and coordinates, which list is displayed on the screen 58a.

Figure 7:
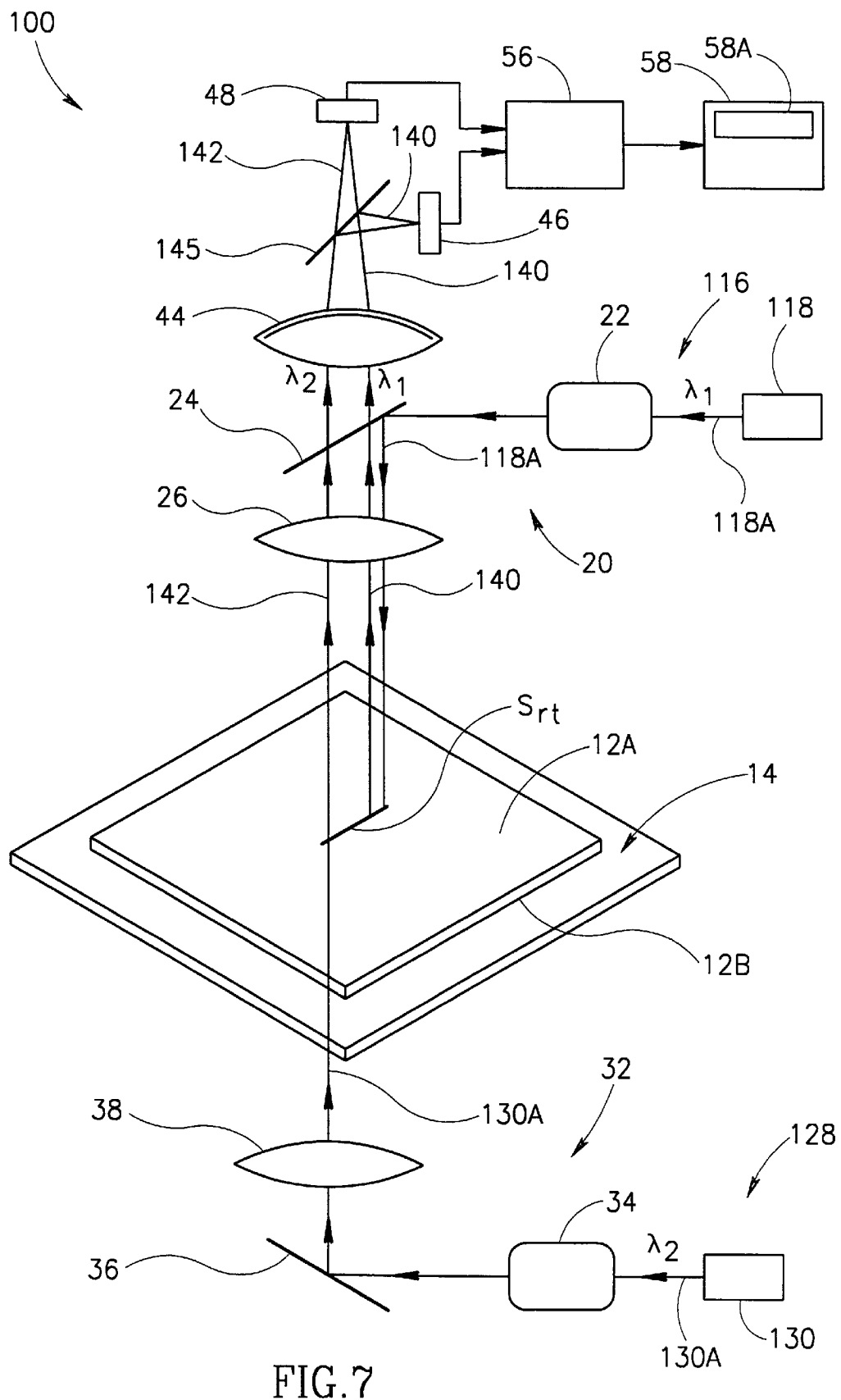
FIG. 7 is a block diagram illustrating the main components of an inspection apparatus, according to another embodiment of the invention.

Reference is now made to FIG. 7 illustrating the main components of an apparatus, generally designated 100, which is constructed and operated according to another embodiment of the present invention. Those components which are identical in the apparatuses 10 and 100 are indicated by the same reference numbers, in order to facilitate understanding. The apparatus 100 inspects the photomask 12 supported on the sliding frame 14. Two illumination assemblies 116 and 128 are provided for illuminating the upper surface 12a of the photomask 12 from its opposite sides. The assemblies 116 and 128 are generally similar to those of the apparatus 10, each comprising a light source for emitting a beam of incident radiation and a suitable optical system accommodated in the optical path of the emitted beam. In distinction to the apparatus 10, the light sources 118 and 130 produce, respectively, light beams 118a and 130a of different wavelengths $\lambda_1$ and $\lambda_2$. The beam 118a is directed through the optical system 20 onto the surface 12a so as to illuminate a strip St and be reflected from opaque regions, if any, producing a reflected beam 140. The light beam 130a, in turn, passes through the optical system 32 so as to impinge onto the surface 12a and illuminate the same strip $S_{rt}$, producing a transmitted beam 142. The reflected and transmitted beams 140 and 142 are projected via an optical system 144 onto the image sensors 46 and 48, respectively. To this end, the system 144, in addition to the collecting lens 44, comprises a dichroic beam splitter 145. The dichroic beam splitter is a well known color-selective device which is widely used for transmitting a particular band of spectral energy and reflecting any other.

It will be readily understood, although not specifically shown, that the operation of the apparatus 100 is generally similar to that of the apparatus 10. Each illuminated strip St is projected by the optical system 144 into two imaged lines (not shown). The photomask 12 is sequentially displaced along the axis y a certain preset step. It is appreciated that this step is, preferably, equal to the width of the imaged line so as to, on the one hand, avoid an overlap between the images and, on the other hand, speed up the inspection. Upon inspecting a slice of the photomask, the latter is displaced along the axis x a certain step which is, preferably, equal to the length of the imaged line.

Figure 8:
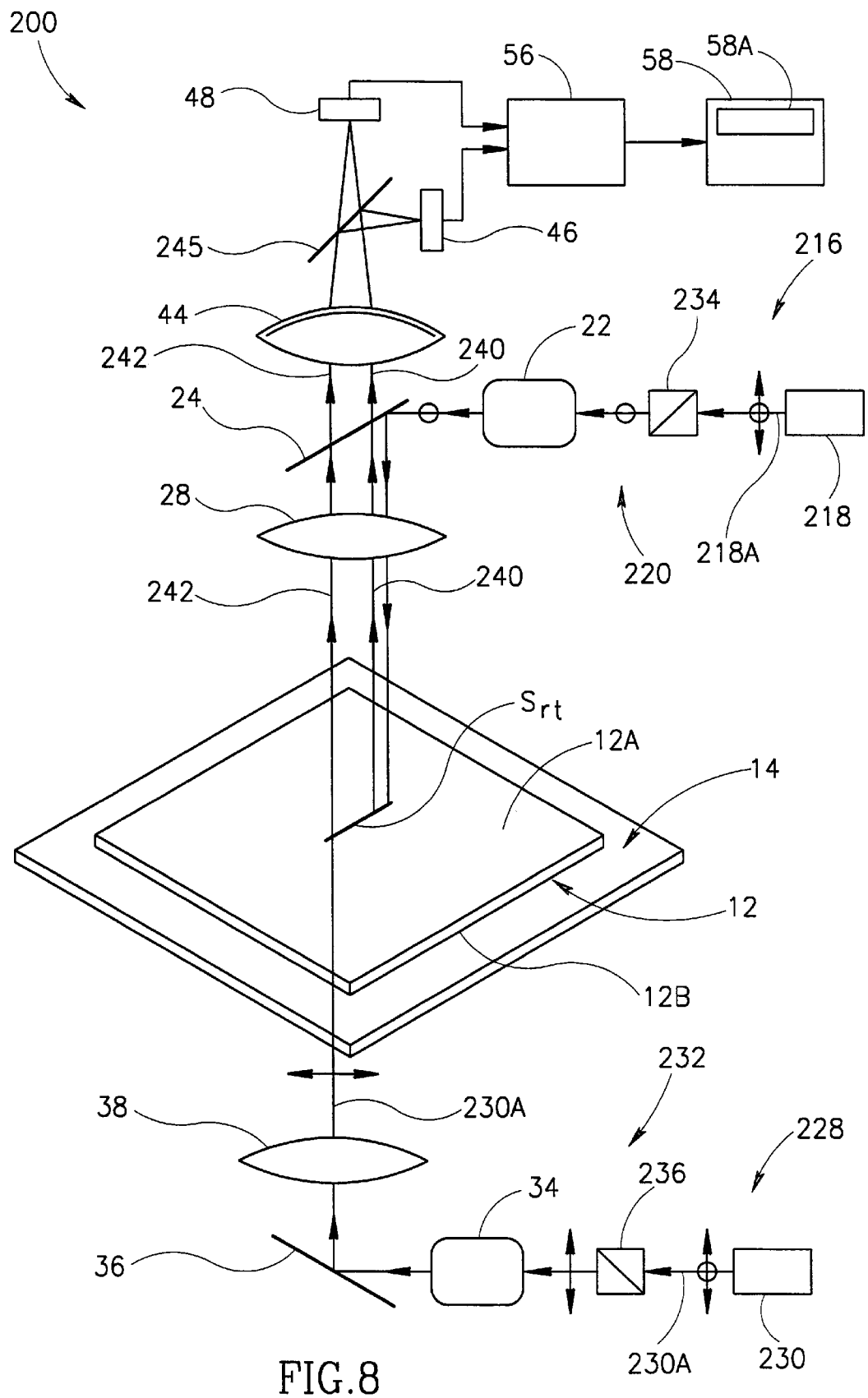
FIG. 8 is a block diagram illustrating the main components of an inspection apparatus, according to yet another embodiment of the invention.

Referring to FIG. 8, there is illustrated an apparatus 200 constructed and operated according to yet another embodiment of the invention. Similarly, those components which are identical in the above is described embodiments and the apparatus 200 are indicated by the same reference numbers. The apparatus 200 is capable of illuminating a strip S of the upper surface 12a of the photomask 12 by two beams of incident radiation 218a and 230a having different polarizations. To this end, the optical systems 220 and 232 comprise beam polarizer devices 234 and 236 accommodated in the optical paths of the beams 218a and 230a, respectively. Alternatively, each of the light sources 218 and 230 may be of a kind adapted for producing a polarized light beam. Hence, reflected and transmitted beams 240 and 242 are of different polarizations. The dichroic beam splitter 145 of FIG. 7 is replaced by a beam polarizer device 245 of a kind capable of splitting the different polarizations. Such beam polarizer devices are known, typically comprising a polarization sensitive medium, for example, in the form of a birefringent cell or multi-layered dielectric structure. It is appreciated that light component returned from a foreign particle located in the opaque region of the upper surface of the photomask, would be, due to reflection and diffraction effects, a depolarized scattered forward light. This increases the contrast of particle's appearance on the bright background in the 'reflected' image.

Those skilled in the art will readily appreciate that various modifications and changes may be applied to the preferred embodiments of the invention as hereinbefore exemplified without departing from its scope as defined in and by the appended claims. In the method claims which follow, characters which are used to designate claim steps are provided for convenience only and do not apply any particular order of performing the steps.

What is claimed is:

1. A method for inspecting an object having upper and lower faces for detecting defects existing on the object, the method comprising:
   a) providing first and second beams of radiation;
   b) directing the first beam of radiation onto the object so as to illuminate a first area of the object, and sensing a light component reflected from one face of the object;
   c) directing the second beam of radiation onto the object so as to illuminate a second, different area of the object, and sensing a light component transmitted through the upper and lower faces of the object;
   d) simultaneously acquiring first and second images of the object, wherein the first image is formed by the reflected light component and the second image is formed by the transmitted light component; and
   e) analyzing said first and second images so as to provide data indicative of said defects.

2. The method according to claim 1, wherein acquiring the first and second images comprises directing the reflected and transmitted light components onto first and second image sensors, respectively.

3. The method according to claim 2, wherein the first and second beams of the radiation are directed onto the object from the opposite faces thereof, and further comprising:
   directing the reflected and transmitted light components via an optical system mounted in optical paths of the reflected and transmitted light components onto the first and second image sensors accommodated at one side of the object.

4. The method according to claim 1, wherein directing the first and second beams of the radiation onto the object further comprise manipulating said first and second beams of the radiation to illuminate first and second parallel spaced-apart corresponding portions of the object.

5. The method according to claim 4, wherein each of said first and second portions of the object are in the form of a strip.

6. The method according to claim 4, wherein
   the first and second beams of the radiation are directed onto the object from the opposite faces thereof;
   the reflected and transmitted light components are directed onto, respectively, first and second image sensors, accommodated at one side of the object, via an optical system mounted in optical paths of the reflected and transmitted light components; and
   the first and second portions extend symmetrically relative to an optical axis of said optical system.

7. The method according to claim 1, wherein
   the first and second beams of the radiation are directed onto the object from the opposite faces thereof; and
   the first and second beams of the incident radiation are formed of light having different wavelengths.

8. The method according to claim 1, wherein
   the first and second beams of the radiation are directed onto the object from the opposite faces thereof;
   the first and second beams of the radiation are formed of light having different polarizations.

9. The method according to claim 4, wherein the first and second images of the first and second portions are in the form of two lines, each having a width "a" and a length "b", the width "a" being substantially smaller than the width of the respective portion, a space "d" between lines being such as to satisfy the following condition:

$$d = n \cdot a$$

wherein "n" is an integer such $n \geq 1$.

10. The method according to claim 1, wherein the step of providing the first and second beams of the radiation comprises providing first and second light sources each generating a beam of light.

11. The method according to claim 1, wherein the step of providing the first and second beams of the radiation comprises providing a light source generating a beam of light and directing the generated beam of light towards the object via a beam splitter, which splits the generated beam of light into the first and second beams of the radiation.

12. The method according to claim 1, further comprising the step of:
   supporting the object for sliding movement along two orthogonally oriented axes within an inspection plane so as to provide said first and second images of each point of the object.

13. The method according to claim 1, wherein the analyzing of the first and second images comprises comparing the images to each other.

14. An apparatus for optical inspection of an object, having upper and lower faces, so as to detect defects existing on the object, the apparatus comprising:
   i. an illumination system providing first and second beams of radiation simultaneously directed respectively onto a first area of the object and a second, different area of the object;
   ii. a sensing system mounted in the vicinity of the object and simultaneously sensing a light component of the first beam reflected from the upper face of the object and a light component of the second beam transmitted through the upper and lower faces of the object and providing output signals representative thereof;
   iii. a light directing system directing the reflected and transmitted light components onto the sensing system; and
   iv. a processor coupled to the sensing system for receiving the output signals; representative of the reflected and transmitted light components and for analyzing the signals so as to provide data indicative of said defects.

15. The apparatus according to claim 14, wherein the illumination system comprises two light sources for generating, respectively, said first and second beams of the radiation.

16. The apparatus according to claim 14, wherein the illumination system comprises a light source for generating a beam of light and a beam splitter for splitting the generated beam into said first and second beams of the radiation.

17. The apparatus according to claim 14, wherein the illumination system comprises a directing optics for directing the first and second beams of the radiation onto, respectively, the opposite faces of the object.

18. The apparatus according to claim 14, wherein the illumination system comprises a directing optics for directing the first and second beams of the radiation onto, respectively, first and second parallel, spaced-apart portions of the object.

19. The apparatus according to claim 14, wherein said first and second beams of the radiation are formed of light of different wavelengths.

20. The apparatus according to claim 14, wherein said first and second beams of the radiation are formed of light of different polarizations.

21. The apparatus according to claim 14, wherein the sensing system comprises first and second image sensors for detecting, respectively, the reflected and transmitted light components.

22. The apparatus according to claim 17, wherein the light directing optics and the sensing system are accommodated at one side of the object.

23. The apparatus according to claim 14, and also comprising a support base for supporting the object for sliding movement along two orthogonally oriented axes within an inspection plane.

24. The method according to claim 1, wherein simultaneously acquiring first and second images of the object comprises directing the reflected light component to a first sensor located on a first side of the object and directing the transmitted light component to a second sensor located on said first side of the object.

25. The method according to claim 1, wherein simultaneously acquiring first and second images of the object comprises directing the reflected light component to a first multi-element sensor and directing the transmitted light component to a second multi-element sensor.

26. The method according to claim 25, wherein said first multi-element sensor is a first charge coupled device (CCD) having a plurality of pixels, and said second multi-element sensor is a second charge coupled device (CCD) having a plurality of pixels.

27. The method according to claim 25, wherein said first multi-element sensor is a first time delay integration (TDI) sensor, and said second multi-element sensor is a second time delay integration (TDI) sensor.

28. A method for inspecting an object having upper and lower faces for detecting defects existing on the object, said method comprising:
   a) providing first and second beams of radiation;
   b) directing the first beam of radiation onto the object and sensing a light component reflected from one face of the object;
   c) directing the second beam of radiation onto the object and sensing a light component transmitted through the upper and lower faces of the object;
   d) simultaneously acquiring first and second images of the object, wherein the first image is formed by directing the reflected light component to a first sensor located on a first side of the object and the second image is formed by directing the transmitted light component to a second sensor located on said first side of the object; and
   e) analyzing said first and second images so as to provide data indicative of said defects.

29. The method according to claim 28, wherein directing said first and second beams comprises directing said first beam so as to illuminate a first area of the object and directing said second beam so as to illuminate a second, different area of the object.

30. The method according to claim 28, wherein simultaneously acquiring first and second images of the object comprises directing the reflected light component to a first multi-element sensor and directing the transmitted light component to a second multi-element sensor.

31. The method according to claim 30, wherein said first multi-element sensor is a first charge coupled device (CCD) having a plurality of pixels, and said second multi-element sensor is a second charge coupled device (CCD) having a plurality of pixels.

32. The method according to claim 30, wherein said first multi-element sensor is a first time delay integration (TDI) sensor, and said second multi-element sensor is a second time delay integration (TDI) sensor.

33. The method according to claim 28, wherein the first and second beams of radiation are directed onto the object from opposite faces thereof, and are formed of light having different wavelengths.

34. The method according to claim 28, wherein the first and second beams of radiation are directed onto the object from opposite faces thereof, and are formed of light having different polarizations.

35. An apparatus for optical inspection of an object, having upper and lower faces, so as to detect defects existing on the object, the apparatus comprising:
   i. an illumination system providing first and second beams of radiation simultaneously directed onto the object;
   ii. a sensing system mounted in the vicinity of the object and comprising a first sensor located on a first side of the object and a second sensor located on said first side of the object for simultaneously sensing a light component of the first beam reflected from the upper face of the object and a light component of the second. beam transmitted through the upper and lower faces of the object and providing output signals representative thereof;

iii. a light directing system directing the reflected and transmitted light components; onto the sensing system; and iv. a processor coupled to the sensing system for receiving the output signals representative of the reflected and transmitted light components and for analyzing the signals so as to provide data indicative of said defects.

36. The apparatus according to claim 35, wherein said illumination system provides said first and second beams of radiation respectively onto a first area of the object and a second, different area of the object.

37. The apparatus according to claim 35, wherein each of said first and second sensors comprises a respective multi-element sensor.

38. The apparatus according to claim 35, wherein each of said first and and second sensors comprises a respective charge coupled device (CCD) having a plurality of pixels.

39. The apparatus according to claim 35, wherein each of said first and and second sensors comprises a respective time delay integration (TDI) sensor.

40. The apparatus according to claim 35, wherein said first and second beams of radiation are formed of light of different wavelengths.

41. The apparatus according to claim 35, wherein said first and second beams of radiation are formed of light of different polarizations.

42. A method for inspecting an object having upper and lower faces for detecting defects existing on the object, said method comprising:

a) providing first and second beams of radiation;

b) directing the first beam of radiation onto the object and sensing a light component reflected from one face of the object;

c) directing the second beam of radiation onto the object and sensing a light component transmitted through the upper and lower faces of the object;

d) simultaneously acquiring first and second images of the object, wherein the first image is formed by directing the reflected light component to a first multi-element sensor and the second image is formed by directing the transmitted light component to a second multi-element sensor; and analyzing said first and second images so as to provide data indicative of said defects.

43. The method according to claim 42, wherein simultaneously acquiring first and second images of the object comprises directing the reflected light component to said first multi-element sensor located on a first side of the object and directing the transmitted light component to said second multi-element sensor located on said first side of the object.

44. The method according to claim 42, wherein directing said first and second beams comprises directing said first beam so as to illuminate a first area of the object and directing said second beam so as to illuminate a second, different area of the object.

45. The method according to claim 42, wherein simultaneously acquiring first and second images of the object comprises directing the reflected light component to a first charge coupled device (CCD) and directing the transmitted light component to a second charge coupled device (CCD).

46. The method according to claim 42, wherein simultaneously acquiring first and second images of the object comprises directing the reflected light component to a first time delay integration (TDI) sensor and directing the transmitted light component to a second time delay integration (TDI) sensor.

47. The method according to claim 42, wherein providing first and second beams of radiation comprises providing first and second beams formed of light of different wavelengths.

48. The method according to claim 42, wherein providing first and second beams of radiation comprises providing first and second beams formed of light of different polarizations.

49. An apparatus for optical inspection of an object, having upper and lower faces, so as to detect defects existing on the object, the apparatus comprising:

i. an illumination system providing first and second beams of radiation simultaneously directed onto the object;

ii. a sensing system mounted in the vicinity of the object and comprising first and second sensors each comprising a respective multi-element sensor, said first and second sensors respectively and simultaneously sensing a light component of the first beam reflected from the upper face of the object and a light component of the second beam transmitted through the upper and lower faces of the object and providing output signals representative thereof;

iii. a light directing system directing the reflected and transmitted light components onto the sensing system; and iv. a processor coupled to the sensing system for receiving the output signals representative of the reflected and transmitted light components and for analyzing the signals so as to provide data indicative of said defects.

50. The apparatus according to claim 49, wherein said illumination system provides. said first and second beams of radiation respectively onto a first area of the object and a second, different area of the object.

51. The apparatus according to claim 49, wherein said first and second sensors are located on the same side of the object.

52. The apparatus according to claim 49, wherein said first and second sensors comprise respective charge coupled devices (CCD).

53. The apparatus according to claim 49, wherein said first and second sensors comprise respective time delay integration (TDI) sensors.

54. The apparatus according to claim 49, wherein said illumination system provides first and second beams of radiation of different wavelengths.

55. The apparatus according to claim 49, wherein said illumination system provides first and second beams of radiation of different polarizations.

* * * * *